Jan. 19, 1937. E. A. McILHENNY Plant Pat. 224
CAMELLIA
Filed Aug. 7, 1936
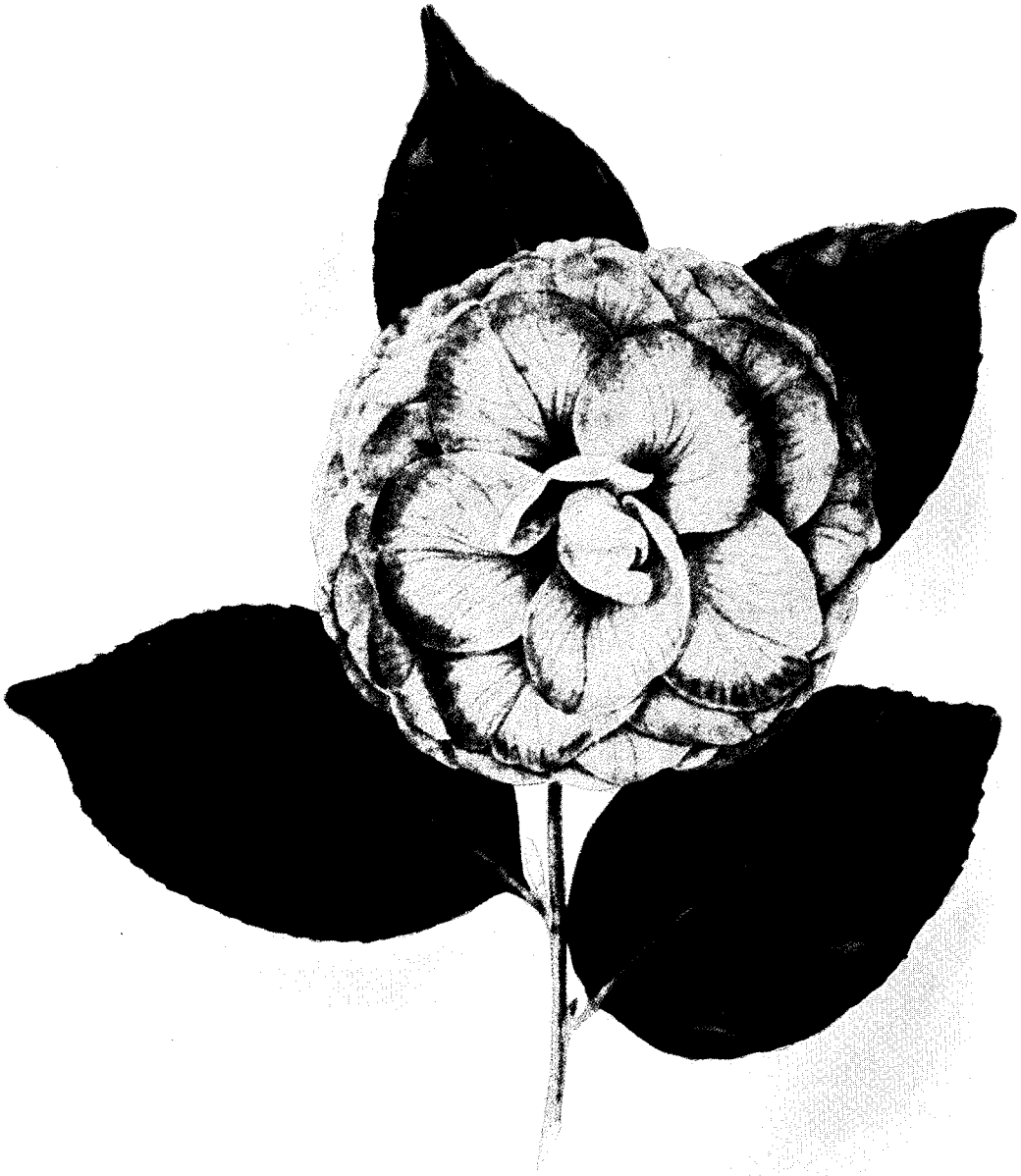
Inventor
E. A. McIlhenny
By Robert Robb
Attorneys Patented Jan. 19, 1937

Plant Pat. 224

UNITED STATES PATENT OFFICE

224

CAMELLIA

Edward A. McIlhenny, Avery Island, La.

Application August 7, 1936, Serial No. 94,873

1 Claim. (Cl. 47—60)

The present discovery relates to a new and distinct variety of *Camellia japonica*—a sport of the known variety "Reine des Fleurs".

The new variety shrub is characterized as to novelty by its exceptionally large blossom and exceptionally deep red color at the base. Primarily, however, it is distinguished from all others, so far as I am aware, by the distinct purple cast overlying the red, from the center of the petals to the ends, giving the general impression of a purple blossom.

It may be noted that the new plant herein described is distinguished from its parent in that the blossom of the new variety is much larger, the petals being at least twice, or more, the size of those of the parent variety, and a much deeper red color. Of course, the main distinguishing feature is the purple overcast. Furthermore, the foliage of the new variety is narrower and longer than that of its parent.

The foregoing characteristics of the blossom have been found by asexual reproduction to be fixed.

The following is a detail description of this new variety, all reference to color conforming to Ridgway's color standard or else to the ordinary dictionary definitions:—

Parentage:
Sport of Reine des Fleurs.
Classification:
Botanic—*Camellia japonica*.

*Flower*

Blooming habit:
Blooms profusely in midseason.
Blossoms opening from early December to mid-March.
Continuous.
Bud:
*Size*.—Large.
*Form*.—Globular.
*Color*.—A combination of crimson and geranium red of a brilliant hue blending to violet purple at about halfway on outer half of petal.
*Sepals*.—Smooth.
*Calyx*.—Large, smooth.
Bloom:
*Size*.—Very large, 4½"–6" when fully expanded.
*Borne*.—Singly.
*Stems*.—Strong.
*Form*.—Flat with high center.
*Petalage*.—Very double, fully imbricated. Stamens hidden. Number of petals about sixty.
*Color*.—Very deep red with purple overcast from center of petals to ends when freshly opened, dulling somewhat with age.
Petals:
*Texture*.—Thick, leathery.
*Appearance*.—Upper surface—satiny. Under surface—shiny.
*Form*.—Round.
*Arrangement*.—Imbricated.
*Fragrance*.—None.
*Lasting quality*.—On the plant and as cut flower very long.
Genital organs:
Completely hidden by inner petals.
Undeveloped.
Fruit:
None.

*Plant*

Form:
Shrub.
Growth:
Vigorous.
Upright, branching.
Foliage:
*Size*.—Very large.
*Quantity*.—Abundant.
*Color*.—New foliage—maroon fading to brick red at juncture of leaves. New leaves olive drab veined malachite green. Old foliage—upper side glossy normal green. Under side dull. Paler than upper side.
*Shape*.—Oval-pointed.
*Texture*.—Leathery, glossy, smooth. Ribs and veins prominent.
*Edge*.—Serrated, small.
*Rachis*.—Colored gray green.
*Disease resistance*.—Good.
Wood:
*New wood*.—Color—maroon fading to brick red at leaf joints. Bark—smooth.
*Old wood*.—Color—brown. Bark—smooth.

I claim:

A new and distinct variety of *Camellia japonica* characterized as to novelty by the unusual size and the distinctive color of its bud and bloom, substantially as shown and described.

EDWARD A. McILHENNY.